(12) United States Patent
Singletary et al.

(10) Patent No.: US 10,247,522 B2
(45) Date of Patent: Apr. 2, 2019

(54) COMPOSITE BALLISTIC RESISTANT LAMINATE

(71) Applicant: E I DU PONT DE NEMOURS AND COMPANY, Wilmington, DE (US)

(72) Inventors: James Neal Singletary, Midlothian, VA (US); Leopoldo Alejandro Carbajal, Newark, DE (US); William George Kampert, Wilmington, DE (US); Timothy A Libert, Hockessin, DE (US); Bryan Benedict Sauer, Wilmington, DE (US); Kenneth C Harding, Boone, NC (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 223 days.

(21) Appl. No.: 15/133,283

(22) Filed: Apr. 20, 2016

(65) Prior Publication Data

US 2016/0243790 A1    Aug. 25, 2016

Related U.S. Application Data

(63) Continuation-in-part of application No. 14/709,627, filed on May 12, 2015, now Pat. No. 9,982,967.
(Continued)

(51) Int. Cl.
*B32B 7/00* (2006.01)
*F41H 5/04* (2006.01)
(Continued)

(52) U.S. Cl.
CPC .............. *F41H 5/04* (2013.01); *B32B 5/02* (2013.01); *B32B 5/12* (2013.01); *B32B 7/00* (2013.01);
(Continued)

(58) Field of Classification Search
CPC ........... B32B 2250/00; B32B 2250/05; B32B 2250/40; B32B 2250/42; B32B 2255/02;
(Continued)

(56) References Cited

U.S. PATENT DOCUMENTS

| 4,309,487 A | 1/1982 | Holmes |
| 6,689,412 B1 | 2/2004 | Bourrieres |

(Continued)

FOREIGN PATENT DOCUMENTS

WO    2015/022234 A1    2/2015

OTHER PUBLICATIONS

International Search Report, dated Dec. 15, 2016, for International Application PCT/US2016/032699, filed on May 16, 2016, ISA European Patent Office, Jan Boon, authorized officer.
(Continued)

*Primary Examiner* — Lawrence D Ferguson

(57) ABSTRACT

An unconsolidated impact and penetration resistant laminate comprises a plurality of cross-plied sheets, each cross-plied sheet further comprising (i) first and second layers of fibrous or non-fibrous ultra-high molecular weight polyethylene and (ii) first and second layers of thermoplastic adhesive, each adhesive layer having a basis weight of no greater than 5 gsm, wherein (a) the layers of polyethylene and thermoplastic adhesive alternate within the sheet,
(b) at least 50 percent of the polyethylene layers are arranged such that the orientation of the first polyethylene layer is offset with respect to the orientation of the second polyethylene layer, and
(c) the plurality of cross-plied sheets form a stack that, when subjected to compaction at a pressure of 255 bar and a temperature of 132 degrees C., will not suffer a
(Continued)

pressure loss greater than 8 bar within the first two minutes as measured by Test Method B.

20 Claims, 1 Drawing Sheet

Related U.S. Application Data which is a continuation-in-part of application No. 14/625,193, filed on Feb. 18, 2015, now abandoned.

(51) Int. Cl.
| | |
|---|---|
| *B32B 5/12* | (2006.01) |
| *B32B 7/12* | (2006.01) |
| *B32B 27/08* | (2006.01) |
| *B32B 27/32* | (2006.01) |
| *B32B 7/02* | (2019.01) |
| *B32B 7/04* | (2019.01) |
| *B32B 27/06* | (2006.01) |
| *B32B 27/18* | (2006.01) |
| *B32B 27/20* | (2006.01) |
| *B32B 37/06* | (2006.01) |
| *B32B 37/08* | (2006.01) |
| *B32B 37/10* | (2006.01) |
| *B32B 37/12* | (2006.01) |
| *G01N 3/30* | (2006.01) |
| *B32B 5/02* | (2006.01) |
| *B32B 27/12* | (2006.01) |

(52) U.S. Cl.
CPC ............... *B32B 7/005* (2013.01); *B32B 7/02* (2013.01); *B32B 7/04* (2013.01); *B32B 7/12* (2013.01); *B32B 27/06* (2013.01); *B32B 27/08* (2013.01); *B32B 27/12* (2013.01); *B32B 27/18* (2013.01); *B32B 27/20* (2013.01); *B32B 27/32* (2013.01); *B32B 37/06* (2013.01); *B32B 37/08* (2013.01); *B32B 37/10* (2013.01); *B32B 37/12* (2013.01); *F41H 5/0478* (2013.01); *G01N 3/30* (2013.01); *B32B 2250/00* (2013.01); *B32B 2250/05* (2013.01); *B32B 2250/40* (2013.01); *B32B 2250/42* (2013.01); *B32B 2255/02* (2013.01); *B32B 2255/10* (2013.01); *B32B 2255/26* (2013.01); *B32B 2262/0253* (2013.01); *B32B 2264/00* (2013.01); *B32B 2264/02* (2013.01); *B32B 2264/10* (2013.01); *B32B 2307/51* (2013.01); *B32B 2307/514* (2013.01); *B32B 2307/516* (2013.01); *B32B 2307/542* (2013.01); *B32B 2307/558* (2013.01); *B32B 2307/581* (2013.01); *B32B 2307/732* (2013.01); *B32B 2307/734* (2013.01); *B32B 2309/02* (2013.01); *B32B 2309/04* (2013.01); *B32B 2309/12* (2013.01); *B32B 2323/04* (2013.01); *B32B 2571/00* (2013.01); *B32B 2571/02* (2013.01); *G01N 2203/001* (2013.01); *G01N 2203/0232* (2013.01)

(58) Field of Classification Search
CPC ............ B32B 2255/10; B32B 2255/26; B32B 2262/0253; B32B 2264/00; B32B 2264/02; B32B 2264/10; B32B 2307/51; B32B 2307/514; B32B 2307/558; B32B 2307/581; B32B 2307/732; B32B 2307/734; B32B 2309/02; B32B 2309/04; B32B 2309/12; B32B 2323/04; B32B 2571/00; B32B 2571/02; B32B 27/06; B32B 27/08; B32B 27/12; B32B 37/06; B32B 37/08; B32B 37/10; B32B 37/12; B32B 5/02; B32B 5/12; B32B 7/00; B32B 7/005; B32B 7/02; B32B 7/04; B32B 7/12; G01N 2203/001; G01N 2203/0232; G01N 3/30
See application file for complete search history.

(56) References Cited

U.S. PATENT DOCUMENTS

| | | |
|---|---|---|
| 7,923,094 B1 | 4/2011 | Harding et al. |
| 7,972,679 B1 | 7/2011 | Lyons et al. |
| 7,976,932 B1 | 7/2011 | Lyons et al. |
| 7,993,715 B2 | 8/2011 | Geva et al. |
| 8,197,935 B2 | 6/2012 | Bovenschen et al. |
| 2006/0047046 A1* | 3/2006 | Haas ..................... B82Y 30/00 524/432 |
| 2006/0051577 A1 | 3/2006 | Tam et al. |
| 2007/0106046 A1* | 5/2007 | Bruchmann ....... C08G 18/3278 528/44 |
| 2011/0083415 A1 | 4/2011 | Marissen et al. |
| 2011/0266710 A1 | 11/2011 | Tam et al. |
| 2012/0207966 A1 | 8/2012 | Dickson |

OTHER PUBLICATIONS

International Search Report for International Application No. PCT/US2016/014694, filed Jan. 25, 2016; dated May 9, 2016; European Patent Office, authorized officer Andrew Hammond.

\* cited by examiner

COMPOSITE BALLISTIC RESISTANT LAMINATE

RELATED APPLICATION

This application is a continuation-in-part of application Ser. No. 14/709,627 filed on May 12, 2015 which in turn is a continuation-in-part of application Ser. No. 14/625,193 filed on Feb. 18, 2015.

BACKGROUND

1. Field of the Invention

This invention pertains to an impact and penetration resistant laminate suitable for use in hard armor.

2. Description of Related Art

U.S. Pat. No. 4,309,487 to Holmes describes a laminated armor structure consisting of one or more plies of unidirectionally oriented polyethylene film or fibers which are positioned so that the lines of orientation of adjacent units are at angles to each other. Bonding of the plies is achieved solely through the application of heat and pressure to the composite of positioned plies.

U.S. Pat. No. 7,972,679 to Lyons et al discloses a ballistic-resistant molded article having a sandwich-type structure including two outer portions of a first high modulus material surrounding an inner portion of a second high modulus material. The outer portions are comprised of a plurality of interleaved layers of adhesive coated cross-plied non-fibrous ultra-high molecular weight polyethylene tape. The inner portion is comprised of a plurality of interleaved layers of high modulus cross-plied fibers embedded in resin. The stack of interleaved layers is compressed at high temperature and pressure to form a hybrid sandwich ballistic-resistant molded article that includes a mix of high modulus materials. It has been found that ballistic resistance is higher for the hybrid structure than for a monolithic structure of comparable areal density.

U.S. Pat. No. 7,976,932 to Lyons et al teaches a ballistic resistant panel including a strike face portion and a backing portion. The strike face portion includes a plurality of interleaved layers of non-fibrous ultra-high molecular weight polyethylene tape. The backing portion includes a plurality of interleaved layers of cross-plied fibers of ultra-high molecular weight polyethylene. The entire stack of interleaved layers is compressed at high temperature and pressure to form a ballistic resistant panel having a strike face on one side. It was been found that ballistic resistance increases as the weight ratio of the strike face portion with respect to the backing portion decreases. A composite panel having a strike face of Tensylon® tape with at most 40% of the total weight of the panel exhibits improved ballistic resistance properties as compared to a monolithic structure of strictly interleaved layers of cross-plied high modulus fibers.

U.S. Pat. No. 8,197,935 to Bovenschen at al discloses a ballistic-resistant moulded article having a compressed stack of sheets including reinforcing elongate bodies, where at least some of the elongate bodies are polyethylene elongate bodies that have a weight average molecular weight of at least 100,000 gram/mole and a Mw/Mn ratio of at most 6.

U.S. Pat. No. 7,993,715 to Geva at al relates to polyethylene material that has a plurality of unidirectionally oriented polyethylene layers cross-plied and compressed at an angle to one another, each polyethylene layer composed of ultra-high molecular weight polyethylene and essentially devoid of resin. The invention further relates to ballistic resistant articles that include or incorporate the inventive polyethylene material and to methods of preparing the material and articles incorporating same.

Ultra-high molecular weight polyethylene continuous filaments or fibers may be produced by a gel spinning process. A plurality of such filaments may then be combined to form a yarn. Such multi-filament yarns are available from Honeywell International Inc. or DSM under the tradenames SPECTRA and DYNEEMA respectively. Exemplary patent publications describing this technology are US 2011/0266710, US 2011/083415, US 2006/051577 and U.S. Pat. No. 6,689,412.

The use of an adhesive to provide a bond between two sheets of UHMWPE film is known in the art. However, these adhesive matrices melt between the UHMWPE layers and therefore tend to act as lubricants, making a multi-layer assemblage of sheet and adhesive unstable under manufacturing conditions that require high pressure. When under pressure, the sheets move relative to each other in order to relieve small stress imbalances. If the UHMWPE sheets shift, the finished article's "dimensional stability", that is to say its shape and fitness for use are potentially compromised. Further, sheet slippage can also present a safety issue during production. The dimensional stability of a multi-layer sheet and adhesive assemblage reduces further as the thickness of the assemblage increases. In this context, dimensional stability is a comparison of the shape of the article after molding compared to the shape before molding. Ideally, the two shapes should be the same with no lateral movement. There remains a need therefore to provide a multi-layer sheet and adhesive assemblage in which adjacent sheets will not move relative to each other during a pressing or lamination process.

SUMMARY OF THE INVENTION

This invention pertains to an unconsolidated impact and penetration resistant laminate comprising a plurality of cross-plied sheets, each cross-plied sheet further comprising (i) first and second layers of fibrous or non-fibrous ultra-high molecular weight polyethylene and (ii) first and second layers of thermoplastic adhesive, each adhesive layer having a basis weight of no greater than 5 gsm, wherein (a) the layers of polyethylene and thermoplastic adhesive alternate within the sheet, (b) greater than 50 percent of the polyethylene layers are arranged such that the orientation of the first polyethylene layer is offset with respect to the orientation of the second polyethylene layer, and (c) the plurality of cross-plied sheets form a stack that, when subjected to compaction at a pressure of 255 bar and a temperature of 132 degrees C., will not suffer a pressure loss greater than 8 bar within the first two minutes as measured by Test Method B.

DETAILED DESCRIPTION

Figure 1:
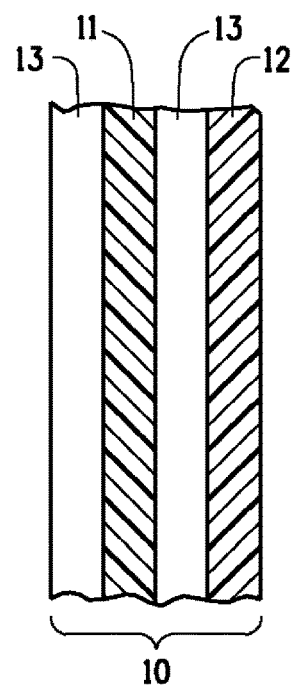
FIG. 1 shows a cross section through a cross-plied sheet.

The date and/or issue of specifications referenced in this section are as follows:

ASTM D 7744-11, "Standard Test Method for Tensile Testing of High Performance Polyethylene Tapes", published September 2011.

ASTM D 4440-07, "Standard Test Method for Plastics: Dynamic Mechanical Properties: Melt Rheology", published March 2007.

Cross-plied Sheet

A cross-plied sheet is shown at 10 in FIG. 1 and comprises first and second layers of ultra-high molecular weight polyethylene, hereinafter UHMWPE, shown as 11 and 12 respectively and first and second layers of a thermoplastic adhesive shown as 13 and 14 respectively. By UHMWPE is meant a film or fiber made from a polyethylene polymer having a viscosity average molecular weight of at least 2 million. In some embodiments the molecular weight is between 2-6 million or even 3-5 million. More preferably, the viscosity average molecular weight is at least 4 million. Examples of suitable polyethylene materials are Ticona GUR from Ticona Engineering Polymers, Auburn Hills, Mich. and Hi-ZEX MILLION™ from Mitsui Chemicals America, Inc., Rye Brook, N.Y.

In the case of a film, each film UHMWPE layer is non-filamentary and is highly oriented. By highly oriented is meant that the modulus in one direction, normally the direction in which the oriented film layer is produced, is at least 10 times greater than in any other direction. Preferably, the modulus in one direction is at least 20 times greater and more preferably at least 30 times greater than in any other direction. The two oriented film layers 11 and 12 in FIG. 1 are combined with adhesive layers 13 and 14 to form a cross-plied sheet 10 in which the orientation of the first UHMWPE layer 11 is offset with respect to the orientation of the second film UHMWPE layer 12. Preferably the two oriented UHMWPE layers 11 and 12 have an orientation that is essentially orthogonal to each other. By "essentially orthogonal" is meant that the two sheets are positioned relative to each other at an angle of 90+/−15 degrees. This is sometimes referred to as a 0/90 arrangement.

First and second thermoplastic adhesive layers 13 and 14 are positioned as shown in FIG. 1. The cross-plied sheet 10 described in FIG. 1 comprises two UHMWPE layers and two adhesive layers. This is a preferred construction, however a sheet may comprise more than two UHMWPE layers or more than two adhesive layers such as in a 0/90/0/90 arrangement in which there are four UHMWPE layers.

The term " film" as used herein refers to UHMWPE products having widths on the order of at least 10 mm or greater, preferably greater than about 20 mm, more preferably greater than about 30 mm and even more preferably greater than about 40 mm of a generally rectangular cross-section and having smooth edges and is specifically used to distinguish from the "fibrous" UHMWPE products that are on the order of 3 mm wide or narrower. The UHMWPE film of the present invention includes a width of at least about 25 mm, a thickness of between 0.03 mm and 0.102 mm, and a first modulus, defined as "M1" in ASTM D7744, of at least about 100 N/Tex, preferably at least about 120 N/Tex, more preferably at least about 140 N/Tex, and most preferably at least about 160 N/Tex. In some embodiments, the film has a very high width to thickness ratio, unlike fibrous UHMWPE, which has a width that is substantially similar to the thickness. A UHMWPE film according to the present invention, for example, may include a width of 25.4 mm and a thickness of 0.0635 mm, which indicates a width to thickness ratio of 400:1. The film may be produced at a linear density of from about 660 Tex to about 1100 Tex and higher. There is no theoretical limit to the width of the high modulus polyethylene film, and it is limited only by the size of the processing equipment. The cross-plied sheet as used herein is meant to refer to thin sections of material in widths greater than about 0.2 m and up to or exceeding 1.6 m width as could be produced in large commercial equipment specifically designed for production in such widths and having a rectangular cross-section and smooth edges.

In the case of UHMWPE filamentary yarns, a layer is formed by aligning together a plurality of yarns such that they form a planar array with the orientation of all yarns, and hence the filaments within the yarn, aligned in the same direction. Such a layer is sometimes referred to as a unidirectional or UD layer. In the sheet, the orientation of one UHMWPE fibrous UD layer is offset, preferably orthogonally with the orientation of the adjacent UHMWPE fibrous UD layer in the sheet.

The UHMWPE layers in the sheet may all be film layers or all fiber layers or some combination of both.

Thermoplastic Adhesive

A thermoplastic adhesive 13 in FIG. 1 is placed between the first and second UHMWPE layers and on one outer surface of one of the UHMWPE layers so as to bond adjacent UHMWPE layers together. In the example of FIG. 1, the first adhesive layer 13 is between the two UHMWPE layers and the second adhesive layer 14 is on the outer surface of the first UHMWPE layer. Each adhesive layer has a basis weight of no greater than 5 gsm and a zero-shear-rate viscosity, when measured at 125° C. by an oscillating disc rheometer, of at least 1500 Pa-s. In some embodiments, the adhesive has a zero-shear-rate viscosity of at least 10,000 Pa-s. In yet other embodiments, the adhesive has a zero-shear-rate viscosity of at least 100,000 Pa-s. In other embodiments, the adhesive has a zero-shear-rate viscosity of at least 1,000,000 Pa-s.

Zero-shear-rate viscosity can be determined by measuring the complex viscosity of an adhesive sample per ASTM D 4440. The adhesive is held at 125° C. in an oscillating disc rheometer, and subjected to oscillation across a frequency sweep from 0.1 rad/s to 100 rad/s. Viscosity as a function of frequency is then fitted to the so-called four parameter Carreau-Yasuda equation:

$$\eta = (\eta_{o,cy})/[1+(T_{cy}\gamma')^a]^{p/a}$$

where $\eta_{o,cy}$ is the Carreau-Yasuda zero-shear-rate viscosity, $T_{cy}$ is the Carreau-Yasuda time constant, p is the Carreau-Yasuda rate constant that describes the slope of the power-law region, and a is the parameter that describes the transition region between the Newtonian region and the power-law region. Multiple frequency sweeps should be performed and averaged before fitting the data to the equation to determine the zero-shear-rate viscosity. Such measurements are known to one skilled in the art of polymer characterization. A suitable rheometer has been found to be an ARES LS2 from TA Instruments, New Castle, Del. A forced convection oven has been found adequate for controlling the adhesive sample temperature. Using this equipment, plate temperature can be calibrated using a disc of perfluoroalkoxy polymer with a thermocouple in the middle. 25 mm diameter plates with smooth surfaces are used for mounting the adhesive sample. Adhesive samples may be variously cast or machined to form the cylindrical sample needed to contact the oscillating plates, depending on the nature of the adhesive. Care should be taken to avoid degrading the adhesive during specimen preparation. An exemplary description of the application of the Carreau-Yasuda model to polymer flow is given in Stephen L. Rosen, Fundamental Principles of Polymeric Materials, John Wiley & Sons, New York, 1982, page 207.

In some embodiments the weight of the adhesive layer is less than 4.5 gsm or even less than 4 gsm.

Suitable examples of adhesive are urethanes, polyethylene, ethylene copolymers including ethylene-octene copolymers, ionomers, metallocenes, and thermoplastic rubbers such as block copolymers of styrene and isoprene or styrene and butadiene. The adhesive may further comprise a thixotrope to reduce the propensity for adjacent sheets to slide relative to each other during a compression process. Suitable thixotropes include organic particles whose shape can be characterized as dendritic (representative of which is DuPont™ Kevlar® aramid fiber pulp), spherical, plate-like, or rod-like, or inorganic particles such as silica or aluminum trihydrate. The adhesive may further include other functional additives such as nanomaterials and flame retardants.

The adhesive may be in the form of a film, paste, liquid or nonwoven scrim.

Impact and Penetration Resistant Laminate

Figure 2:
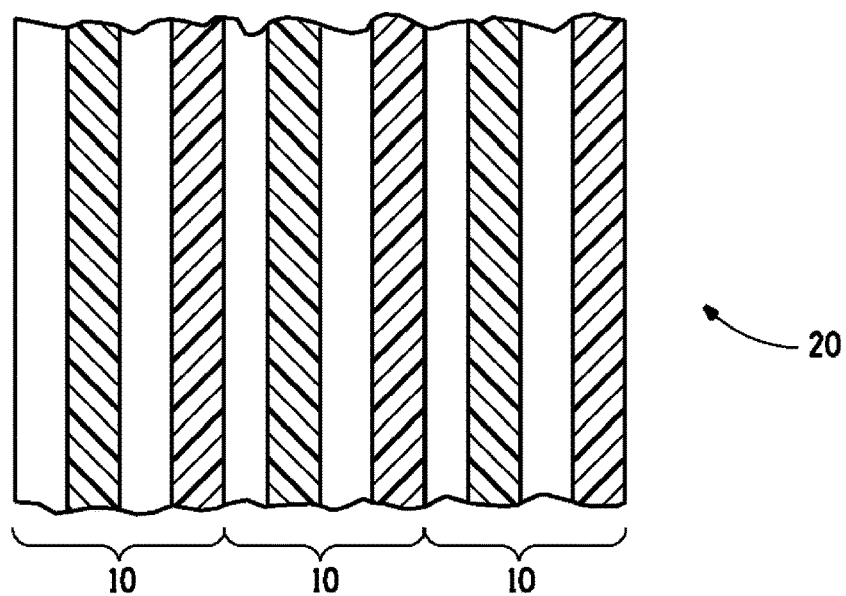
FIG. 2 shows a cross section through a laminate comprising a plurality of cross-plied sheets.

FIG. 2 shows an exemplary laminate comprising a plurality of the cross-plied sheets 10 previously described. In some embodiments, greater than 50 percent, more preferably greater than 75% percent or most preferably greater than 95% or even 100 percent of the sheets are positioned within the laminate such that the orientation of a UHMWPE layer of one sheet is offset with respect to the orientation of the closest UHMWPE layer of an adjacent sheet.

The number of sheets in a laminate will vary based on the design requirements of the finished article but typically is in the range of from 20 to 1000 giving a laminate weight range of from 0.1 to 600 kg/m² or from 1 to 60 kg/m² or even from 1 to 40 kg/m². The laminate is formed by compression of a stack of sheets at a temperature at which the adhesive will flow but is less than the temperature at which the UHMWPE layer of the sheet loses orientation, and thus mechanical strength. Typically the adhesive comprises no more than 15 weight percent of the combined weight of UHMWPE plus adhesive in the laminate.

The laminate may comprise sheets in which all the UHMWPE layers are in the form of a film, or all the UHMWPE layers are in the form of yarns, or there may be some layers that are in the form of film and other layers in the form of filamentary yarns.

The modulus of elasticity through the thickness of the compressed laminate, as measured by Test Method A, is at least 3 GPa. In some embodiments, the modulus of elasticity is at least 3.2 GPa or even at least 3.5 GPa. In another embodiment, the modulus of elasticity is at least 4 GPa. Preferably, the modulus of elasticity through the thickness of the compressed laminate should be no higher than ten times the modulus of elasticity through the thickness of the polyethylene sheet component of the laminate.

A method of making an impact penetration resistant laminate comprises the steps of (i) providing a plurality of cross-plied sheets 10 wherein each sheet comprises two layers of UHMWPE 11 and 12 that are separated by an adhesive layer 13 with a further adhesive layer 14 on the outer surface of one of the UHMWPE layers arranged such that the orientation of one UHMWPE layer 11 is offset with respect to the orientation of the other UHMWPE layer 12, wherein the adhesive has a basis weight of no greater than 5 gsm and a zero-shear-rate viscosity, when measured per ASTM D 4440 at 125° C. in a frequency sweep between 0.1 rad/s and 100 rad/s by an oscillating disc rheometer, and fitted to the four parameter Carreau-Yasuda model, of at least 1500 Pa-s, (ii) assembling a stack 20 comprising a plurality of sheets 10 of step (i) in an arrangement wherein at least 50 percent of the sheets are positioned such that the orientation of a UHMWPE layer of one sheet is offset with respect to the orientation of the closest UHMWPE layer of an adjacent sheet and the combined weight of the stack is from 0.6 to 600 kg/m², (iii) subjecting the stack of step (ii) to a pressure of from 10 to 400 bar and a temperature of from 70 to 150 degrees C. for between 5 and 60 minutes, and (iv) cooling the laminate to a temperature of 25 degrees C. or less.

In some embodiments, the combined weight of the stack of step (ii) is from 1 to 40 kg/m², Under the processing conditions described above, it has been surprisingly found that the impact penetration resistance of the compressed laminate increased at molding temperatures higher than previously taught.

A convenient method to assess suitability of materials for efficacy in the cross-plied sheet 10 and subsequently in the laminate 20 is to subject the assembled stack 20 to a compaction pressure of 255 bar and a temperature of 132 degrees C. and observe whether the stack will suffer a pressure loss greater than 8 bar within the first two minutes. Component materials for the sheet are deemed suitable for purpose if these pressure loss criteria are met. Preferably, the material will suffer a pressure loss of less than 9 Bar or less than 8 Bar, more preferably, less than 7 Bar, yet more preferably, less than 6 Bar, yet more preferably, less than 5-Bar. This is referenced hereinafter as Test Method B.

Test Methods

Test Method A

The modulus of elasticity ($E_3$) through the thickness of a compressed laminate was determined using the speed of sound through the thickness of the part, $C_{33}$. $C_{33}$ may be determined by a low pressure contacting ultrasonic speed of sound measurement. A suitable measuring device is an Opus 3-D ultrasonic stiffness transduction instrument from Soni-Sys, Atlanta, Ga., at default settings. It requires input of the sample areal density, AD, then automatically determines thickness, t, and $C_{33}$ in through thickness transmission at 1-MHz frequency. One skilled in the art could use other devices.

From the measured $C_{33}$ and the density of the part, $\rho$, $E_3$ is calculated as: $E_3 = [C_{33} \, t/AD]^{1/2}$ Test Method B This method provides a means to assess whether a consolidated stack of cross-plied sheets will or will not suffer a pressure loss greater than 8 bar within the first two minutes when subjected to a compaction at a pressure of 255 bar and a temperature of 132 degrees C.

UHMWPE layers as previously described are cut into 50 mm×50 mm squares such that the layers are cut, in the case of a film, in the direction of highest orientation, or, in the case of yarns, along the axis of fiber alignment. Two layers of UHMWPE and two layers of adhesive are assembled as shown in FIG. 1 to form a sheet 10. The orientation of the first UHMWPE layer of the cross-plied sheet is orthogonal to the orientation of the second UHMWPE layer of the cross-plied sheet. A plurality of sheets 10 is assembled into a stack 20 such that the orientation of a UHMWPE layer in one sheet is orthogonal to the orientation of the nearest UHMWPE layer in an adjacent sheet.

The stack should have an areal density of 660+/−50 gsm.

Test Method B requires a press with highly parallel, heated platens, which can be pressurized manually and indicate pressure over time. An example of a suitable press is a Two Post Press Model C from Carver, Inc., Wabash, Ind. The press platens are preheated to 132° C. The pre-prepared stack sample is placed between a layer of thin, heat tolerant release material that will not adhere to the sample or allow adhesive from the sample to flow and foul the platens. Exemplary release material is polyimide film available from E. I. du Pont de Nemours and Company (hereinafter "DuPont"), Wilmington, Del. under the tradename Kapton. The sample is placed in the center of the platen, and a pressure of about 255-bar applied to the sample based on its original 50 mm×50 mm dimensions. The pressure is monitored every minute for five minutes. The pressure is released and the sample removed. The procedure is repeated except that no stack is present and the pressure is monitored for five minutes. Only the release material is between the platens. This measurement gives an indication of the compliance of the press. A plot of the absolute value of the difference between the two pressure versus time curves, shows the compliance of the test material. It has been discovered that samples which show a material compliance of less than about 9-bar pressure loss after two minutes are unlikely to have sheet slip relative to each other during large scale manufacturing of the laminates and provide a laminate having a modulus of elasticity through the thickness of the laminate, as measured by Test Method A, of at least 3 GPa.

All ballistic targets were shot backed by an approximately 13 cm thick block of plastilina modeling clay following the "V50" test protocol described in MIL-STD-662F, issued 18 Dec. 1997. V50 is a statistical measure that identifies the average velocity at which a bullet or a fragment penetrates the armor equipment in 50% of the shots, versus non penetration of the other 50%. The parameter measured is V50 at zero degrees where the degree angle refers to the obliquity of the projectile to the target.

EXAMPLES

The following examples are given to illustrate the invention and should not be interpreted as limiting it in any way. All parts and percentages are by weight unless otherwise indicated. Examples prepared according to the current invention are indicated by numerical values. Control or Comparative Examples are indicated by letters.

In all examples, each sheet comprised two layers of UHMWPE film that were cross-plied in a 0/90 degree orientation and two layers of adhesive such that each UHMWPE layer and each adhesive layer are arranged alternatively. The sheet material was Tensylon® HS grade obtainable from E. I. DuPont de Nemours and Company, Wilmington, Del. having a nominal areal weight of 50 gsm. The sheets were cut into 500 mm×500 mm squares such that the direction of highest orientation in one layer was orthogonal to the direction of highest orientation in the other layer.

A series of materials were evaluated per Test Method B. In the following examples an unconsolidated laminate comprising a plurality of UHMWPE sheets was subjected to the conditions of Test Method B and the pressure loss determined. Some of the comparative examples did not have an adhesive (matrix) layer. Results are shown in Table 1.

Comparative Examples A through D were sheets from DuPont™ Tensylon® HS-grade film layers, cross-plied with no matrix adhesive. The number of sheets were 12, 16, 20 and 24 in A through D respectively. Up to at least 24 layers, the material did not distort visually and complied minimally in terms of pressure drop and load for at least 5-minutes.

Qualitatively, the initially square samples remained square and not obviously damaged, that is, the polyethylene layers did not shift relative to each other. Quantitatively, the pressure drop of the material complying with the load after two minutes is around 5-Bar, independent of the number of layers. This corresponds to a force drop of about 1.3-kN two minutes into the test. This dimensional stability is desirable in a composite material, in which a matrix would provide a durable bond between the adjacent reinforcement layers. Hence, it would be desirable to select a matrix that allowed similar, high dimensional stability and low load compliance.

Comparative Examples E through K are products representative of current commercially available art. DSM Dyneema products are available from DSM Dyneema LLC, Greenville, N.C. All of these materials showed qualitative distortion from their initially square shape upon removal after the conclusion of the test, noted as "shifting" in the table. The change in shape resulted in cracking of the oriented films, and relative displacement of the fibers. In a commercial article, this would be expected to be undesirable, since the molded reinforcement would not be consistent with the original intent. All of the materials showed a quantitative pressure drop of at least 9-Bar using at most 24 layers of reinforcement. This corresponds to a force drop of over 2.2-kN. Generally, as the number of layers of reinforcement increased, the dimensional stability decreased, resulting in more change in shape in the originally square samples, and larger drops in force and corresponding pressure two minutes after the test started.

Comparative Examples L and M demonstrate the challenge of identifying the correct matrix to meet the required need to maintain high dimensional stability and low load compliance. Both used high melt viscosity matrices known to adhere to a polyethylene film layer reinforcement. The film layers used were Tensylon® HS-grade. Both had practical matrix weight contents to manufacture by conventional means, and are similar to the commercial materials shown in Comparative Examples E through K. However, comparative materials L and M did not remain square and hence did not maintain dimensional stability. Quantitatively, their force drop after two minutes in Test Method B was 3.6-kN, corresponding to a pressure drop of 14-Bar.

Example 1 repeated Comparative Example M, but at less than 10% matrix fraction by weight. Example 1 demonstrated good dimensional stability—visually, the sample remained square, and the oriented film reinforcement did not crack. The force drop two minutes into the test was 1.8-kN, which is similar to the force drop of the reinforcement without a matrix. The pressure drop was less than 7-Bar.

Examples 2-4, also based on Tensylon® HS-grade film layers, used a highly neutralized ionomer with very high melt viscosity at the conditions of Test Method B, and less than 10% by weight matrix fraction. In all tests, the samples remained square and undamaged by the test. Even at 24-layers of reinforcement, the force drop and pressure drop at two minutes into the test were consistent with comparative samples A-D: 1.5-kN load drop and 5-Bar pressure drop.

Hence, by selecting an appropriate adhesive and by reducing the matrix fraction to less than 10% by weight of the composite, we provided a polyethylene-reinforced composites that, when tested in Test Method B, was dimensionally stable and did not shift significantly during high pressure compression molding, which is different from the materials of the comparative examples. This enables the compression molding of polyethylene-reinforced composites to high pressure, which is known to be desirable for many end uses.

TABLE 1

A

| Example | Material | R* | Matrix (approximate percent by weight, composition) |
|---|---|---|---|
| Comparative Example A | DuPont ™ Tensylon ® film, cross-plied | Film | none |
| Comparative Example B | DuPont ™ Tensylon ® film, cross-plied | Film | none |
| Comparative Example C | DuPont ™ Tensylon ® film, cross-plied | Film | none |
| Comparative Example D | DuPont ™ Tensylon ® film, cross-plied | Film | none |
| Comparative Example E | DuPont ™ Tensylon ® HSBD30A | Film | 14% LLDPE |
| Comparative Example F | DuPont ™ Tensylon ® HSBD30A | Film | 14%LLDPE |
| Comparative Example G | DSM Dyneema ® HB26 | Fibers | 18% urethane |
| Comparative Example H | DSM Dyneema ® HB26 | Fibers | 18% urethane |
| Comparative Example I | DSM Dyneema ® HB50 | Fibers | 18% styrene-isoprene-styrene copolymer |
| Comparative Example J | DSM Dyneema ® HB2 | Fibers | 18% styrene-isoprene-styrene copolymer |
| Comparative Example K | DSM Dyneema ® HB2 | Fibers | 18% styrene-isoprene-styrene copolymer |
| Comparative Example L | DuPont ™ Tensylon ® film with matrix, cross-plied | Film | 16% DuPont ® Surlyn ® HPD3001 ionomer |
| Comparative Example M | DuPont ™ Tensylon ® film with matrix, cross-plied | Film | 15% DuPont ™ Surlyn ® 8920 ionomer |
| Example 1 | DuPont ™ Tensylon ® film with matrix, cross-plied | Film | 7% DuPont ™ Surlyn ® 8920 ionomer |
| Example 2 | DuPont ™ Tensylon ® film with matrix, cross-plied | Film | 9% Michelman Michem Prime 2960 |
| Example 3 | DuPont ™ Tensylon ® film with matrix, cross-plied | Film | 7% Michelman Michem Prime 2960 |
| Example 4 | DuPont ™ Tensylon ® film with matrix, cross-plied | Film | 7% Michelman Michem Prime 2960 |

B

| Example | N* | V* | Corrected Force at 2-minutes (kN) | Force Drop at 2-min (kN) | Pressure Drop at 2-min (Bar) |
|---|---|---|---|---|---|
| Comparative Example A | 12 | No | 65.4 | 1.3 | 5 |
| Comparative Example B | 16 | No | 65.4 | 1.3 | 5 |
| Comparative Example C | 20 | No | 65.8 | 0.9 | 3 |
| Comparative Example D | 24 | No | 65.4 | 1.3 | 5 |
| Comparative Example E | 12 | Yes | 58.7 | 8.0 | 31 |
| Comparative Example F | 24 | Yes | 41.4 | 25.4 | 97 |
| Comparative Example G | 24 | Slight | 64.5 | 2.2 | 9 |
| Comparative Example H | 28 | Yes | 63.6 | 3.1 | 12 |
| Comparative Example I | 20 | Yes | 46.7 | 20.0 | 77 |
| Comparative Example J | 20 | Yes | 63.2 | 3.6 | 14 |
| Comparative Example K | 24 | Yes | 40.0 | 26.7 | 102 |
| Comparative Example L | 12 | Yes | 63.2 | 3.6 | 14 |
| Comparative Example M | 12 | Yes | 63.2 | 3.6 | 14 |
| Example 1 | 24 | No | 64.9 | 1.8 | 7 |
| Example 2 | 24 | No | 65.4 | 1.3 | 5 |
| Example 3 | 12 | No | 65.4 | 1.3 | 5 |
| Example 4 | 24 | No | 65.4 | 1.3 | 5 |

R* = Reinforcement
N* = Number of Reinforcement Layers
V* = Visual Observation of Shifting The preceding set of examples also suggests that a simple method for evaluating the ability of a composite to maintain dimensional stability in high pressure compression molding is for a sample of only 12-layers of cross plied reinforcement to not change shape from its initial square shape. Several samples were made with dispersion-based matrices, adding particle fillers. Table 2 repeats some of the comparative examples of Table 1, and then shows how the additional of compatible particles (here, Ludox® silica nanospheres from W. R. Grace, Connecticut, USA, supplied in a dispersion) can significantly increase composite dimensional stability, allowing a thicker matrix without the oriented film cracking and changing shape under the load. Comparative Examples A and L are as previously described. Comparative Example N was similar to comparative Example L except that the matrix weight percent was reduced to 14%. Examples 5 and 6 used Tensylon® HS-grade film for the layers.

TABLE 2

| Example | Matrix (percent by weight, composition) | Filler (percent by weight of matrix, type) | V* |
|---|---|---|---|
| Comparative Example A | none | none | No |
| Comparative Example L | 16% DuPont™ Surlyn® HPD3001 ionomer | none | Yes |

TABLE 3

| Example | Compression Molding Conditions Temperature (° C.) | Compression Molding Conditions Pressure (Bar) | D* | Matrix type | Matrix basis weight (g/m²) | Filler type | Filler percent by weight in matrix | V50 of 23.5-kg/m² target impacted by 7.62 × 39-mm PS ball (m/s) | V50 of 9.8-kg/m² target impacted by 7.62-mm fragment simulating projectile (m/s) |
|---|---|---|---|---|---|---|---|---|---|
| Comparative Example O: BAE Systems Tensylon® HSBD31D | 121 | 204 | marginal | Kraton® D1161 with tackifier | 5 | none | none | 836 | 764 |
| Example 7 | 121 | 279 | excellent | Kraton® D1161 | 5 | Anova Aerogel MT1100 | 20% | 959 | 807 |
| Example 8 | | | | | 4 | | | 965 | 844 |

D* = Dimensional Stability

TABLE 2-continued

| Example | Matrix (percent by weight, composition) | Filler (percent by weight of matrix, type) | V* |
|---|---|---|---|
| Comparative Example N | 14% DuPont™ Surlyn® HPD3001 ionomer | none | Slight |
| Example 5 | 18% DuPont™ Surlyn® HPD3001 ionomer | 35% Ludox™ TN-40 nanospheres | No |
| Example 6 | 13% DuPont™ Surlyn® HPD3001 ionomer | 35% Ludox™ TN-40 nanospheres | No |

V* = Visual Observation of Shifting

The ability to stably withstand high pressure compression molding is a benefit in the composites described herein in that it appears to enable higher armor performance. To demonstrate this, Tensylon® HS-grade oriented polyethylene film was coated with Kraton® D1161 styrene-isoprene-styrene copolymer (Kraton Polymers LLC, Houston, Tex., USA) from a solution to 4 or 5-grams per square meter aim matrix weight, then cross plied into square preforms and compression molded. In Examples 7 and 8, the copolymer was loaded with 20% by matrix weight Enova Aerogel MT1100 silica from Cabot Corporation, Boston, Mass. Table 3 shows the articles made. As a comparative example (Example O), Tensylon® HSBD31D made by BAE Systems, Fairfield, Ohio, was also evaluated. It contains 5-gsm of a mixture of Kraton® D1161 and a tackifier. The molding stability of the Tensylon® HSBD31D comparative example was marginal—some panels shifted during molding and were not used. The molding stability of Examples 7 and 8 were excellent and allowed stable molding to elevated pressure without the reinforcement cracking and shifting. To assess ballistic-resistance performance, the samples were shot in a frame and clamp for the mean velocity to barely perforate the panel, or "V50", as noted by perforations in a 20-gage 2024-T3 aluminum witness plate 15-cm behind the target. The inventive examples, molded to pressures not possible with materials representative of the current art, had ballistic resistance higher than materials representative of the prior art. "V50" testing is well understood to one of moderate skill in the art of ballistic impact, and is explained in for example MIL-STD-662. Fragment simulating projectiles are described in MIL-DTL-46593B.

What is claimed is:

1. An unconsolidated impact and penetration resistant laminate comprising a plurality of cross-plied sheets, each cross-plied sheet further comprising (i) first and second layers of fibrous or non-fibrous ultra-high molecular weight polyethylene and (ii) first and second layers of thermoplastic adhesive, each adhesive layer having a basis weight of no greater than 5 gsm, wherein the thermoplastic adhesive has a zero-shear-rate viscosity, as measured by ASTM D 4440, of at least 1500 Pa-s and wherein
   (a) the layers of polyethylene and thermoplastic adhesive alternate within the sheet,
   (b) greater than 50 percent of the polyethylene layers are arranged such that the orientation of the first polyethylene layer is offset with respect to the orientation of the second polyethylene layer, and
   (c) the plurality of cross-plied sheets form a stack that does not suffer a pressure loss greater than 8 bar within the first two minutes of compaction under Test Method B.

2. The laminate of claim 1 wherein the thermoplastic adhesive further comprises a thixotrope.

3. The laminate of claim 1 wherein the first and second polyethylene layers within a cross-plied sheet have an orientation that is essentially orthogonal to each other.

4. The laminate of claim 1, wherein the thermoplastic adhesive has a zero-shear-rate viscosity of at least 10,000 Pa-s.

5. The laminate of claim 2 wherein the thixotrope is an inorganic particle.

6. The laminate of claim 2 wherein the thixotrope is a dendritic polymeric particle.

7. The laminate of claim 1, wherein the thermoplastic adhesive has a zero-shear-rate viscosity of at least 100,000 Pa-s.

8. The laminate of claim 1, wherein the thermoplastic adhesive has a zero-shear-rate viscosity of at least 1,000,000 Pa-s.

9. The material of claim 1, in which the polyethylene is in the form of nonfibrous sheets or films.

10. The laminate of claim 1, wherein each adhesive layer has a basis weight of no greater than 4.5 gsm.

11. The laminate of claim 1, wherein each adhesive layer has a basis weight of no greater than 4.0 gsm.

12. The laminate of claim 1, wherein the number of cross-plied sheets that form the stack is in the range of from 20 to 1000 cross-plied sheets.

13. The laminate of claim 12, wherein the stack has a weight in the range of from 0.1 to 600 kg/m$^2$.

14. The laminate of claim 12, wherein the stack has a weight in the range of from 1 to 40 kg/m$^2$.

15. The laminate of claim 1, wherein the adhesive comprises no more than 15 weight percent of the weight of the stack.

16. The laminate of claim 1, wherein the stack has a modulus of elasticity, as measured by Test Method A, of at least 3 GPa.

17. The laminate of claim 1, wherein the stack has a modulus of elasticity, as measured by Test Method A, of at least 3.5 GPa.

18. The laminate of claim 1, wherein the stack has a modulus of elasticity, as measured by Test Method A, of at least 4 GPa.

19. The laminate of claim 1, wherein the stack suffers a pressure loss less than 6 bar within the first two minutes of compaction under Test Method B.

20. The laminate of claim 1, wherein the stack suffers a pressure loss less than 5 bar within the first two minutes of compaction under Test Method B.

* * * * *